US008470789B2

(12) United States Patent
van Wetering et al.

(10) Patent No.: US 8,470,789 B2
(45) Date of Patent: Jun. 25, 2013

(54) METHOD FOR INDUCING AND ACCELERATING CELLS

(75) Inventors: Sandra van Wetering, Leidschendam (NL); Tanja Denise de Gruijl, Amsterdam (NL); Adriane Marie Kruisbeek, Amsterdam (NL); Rieneke van de Ven, The Hague (NL); Riekeld Johannes Scheper, Amsterdam (NL)

(73) Assignee: DCPrime B.V., Leiden (NL)

( * ) Notice: Subject to any disclaimer, the term of this patent is extended or adjusted under 35 U.S.C. 154(b) by 153 days.

(21) Appl. No.: 12/736,920

(22) PCT Filed: Nov. 12, 2008

(86) PCT No.: PCT/EP2008/065391
§ 371 (c)(1),
(2), (4) Date: Jan. 25, 2011

(87) PCT Pub. No.: WO2009/019320
PCT Pub. Date: Feb. 12, 2009

(65) Prior Publication Data
US 2011/0117051 A1 May 19, 2011

(30) Foreign Application Priority Data
May 19, 2008 (EP) .................................. 08075502

(51) Int. Cl.
*A61K 31/704* (2006.01)
(52) U.S. Cl.
USPC .......................................................... 514/34
(58) Field of Classification Search
None
See application file for complete search history.

(56) References Cited

U.S. PATENT DOCUMENTS

| 2005/0075308 A1* | 4/2005 | Wilson et al. ................... 514/46 |
| 2007/0041954 A1 | 2/2007 | Ichim |

FOREIGN PATENT DOCUMENTS

| WO | WO 2005/026318 A2 | 3/2005 |
| WO | WO 2007/011693 A2 | 1/2007 |
| WO | WO 2009/019320 A2 | 2/2009 |

OTHER PUBLICATIONS

Masterson et al., Blood 100:701-703 (2002).*
Bengala, et al.; Mobilization; Collection, and Characterization of Peripheral Blood Hemopoietic Progenitors after Chemotherapy eith Epirubicin, Paclitaxel, and Granulocyte-Colony Stimulating Factor Administered to Patients with Metastatic Breast Carcinoma; Cancer; Mar. 1, 1998; vol. 82; No. 5; pp. 867-873.
Ferlini, et al.; A New Method to Evaluate in vitro Myelotoxicity of Antitumour Agents in the First Steps of Drug Development; Pharmacology & Toxicology 2001, 89; 231-236.
Ferrari, et al.: Lack of dendritic cell mobilization into the peripheral blood of cancer patients following standard-or high-dose chemotherapy plus granulocyte-colony stimulating factor; Cancer Immunol Immunother: 2003: 52: 359-366.
Neuhaus, et al.; Multiple sclerosis: Mitoxantrone promotes differential effects on immunocompetent cells in vitro; Journal of Neuroimmunology 168 (2005) 128-137.
Zibera, et al.; An epirubicin/paclitaxel combination mobilizes large amounts of hematopoietic progenitor cells in patients with metastatic breast cancer showing optimal response to the same chemotherapy regimen; Haematologica 1999, 84:924-929.
International Search Report and Written Opinion; PCT/EP2008/065391; Feb. 26, 2009.
PCT International Preliminary Report on Patentability, PCT/EP2008/065391 dated Nov. 23, 2010.
Yilmax et al., Activated myeloid dendritic cells accumulate and colocalize with CD3+ T cells in coronary artery lesions in patients with Kawasaki disease, Experimental Molecular Pathology 2007, pp. 93-103, vol. 83, No. 1.
Bernhard et al., Generation of Immunostimulatory Dendritic Cells from Human CD34+ Hematopoietic Progenitor Cells of the Bone Marrow and Peripheral Blood, Cancer Research, 1995, pp. 1099-1104, vol. 55.
Cignetti et al., CD34+ Acute Myeloid and Lymphoid Leukemic Blasts Can Be Induced to Differentiate Into Dendritic Cells, Blood, 1999, pp. 2048-2055, vol. 94.
Westers et al., Rapid generation of antigen-presenting cells from leukaemic blasts in acute myeloid leukaemia, Cancer Immunology, Immunotherapy, 2003, pp. 17-27, vol. 52.
Santegoets et al., In vitro priming of tumor-specific cytotoxic T. lymphocytes using allogeneic dendritic cells derived from the human MUTZ-3 cell line, Cancer Immunology, Immunotherapy, 2006. pp. 1480-1490.
Communication to EPO regarding application 08826916.2 dated Jan. 24, 2011.
Communication to EPO regarding application 08826916.2 dated Jul. 20, 2012.
PCT International Search Report and Written Opinion for PCT/EP2008/065391 dated Feb. 26, 2009.
Communication from EPO regarding application 08826916.2 dated May 11, 2012.

* cited by examiner

*Primary Examiner* — Daniel C Gamett
(74) *Attorney, Agent, or Firm* — TraskBritt

(57) ABSTRACT

The present invention relates to a method for the production of functional dendritic cells wherein CD34 positive cells are contacted with compounds inducing and accelerating the differentiation of these CD34 positive cells into functional dendritic cells. More in particular, the CD34 positive cells are contacted with anthracyclines and/or anthracenediones. In another aspect, the current invention relates to the cells obtainable by the method according to the invention. In a further aspect the current invention relates to the use of compounds such as anthracyclines and/or anthracenediones that induce and accelerate the differentiation of CD34 positive cells into functional dendritic cells in the manufacture of a medicament for inducing an immune response in human in need thereof.

14 Claims, 9 Drawing Sheets

A

B

A

B

C

METHOD FOR INDUCING AND ACCELERATING CELLS

FIELD OF THE INVENTION

Figure 1:
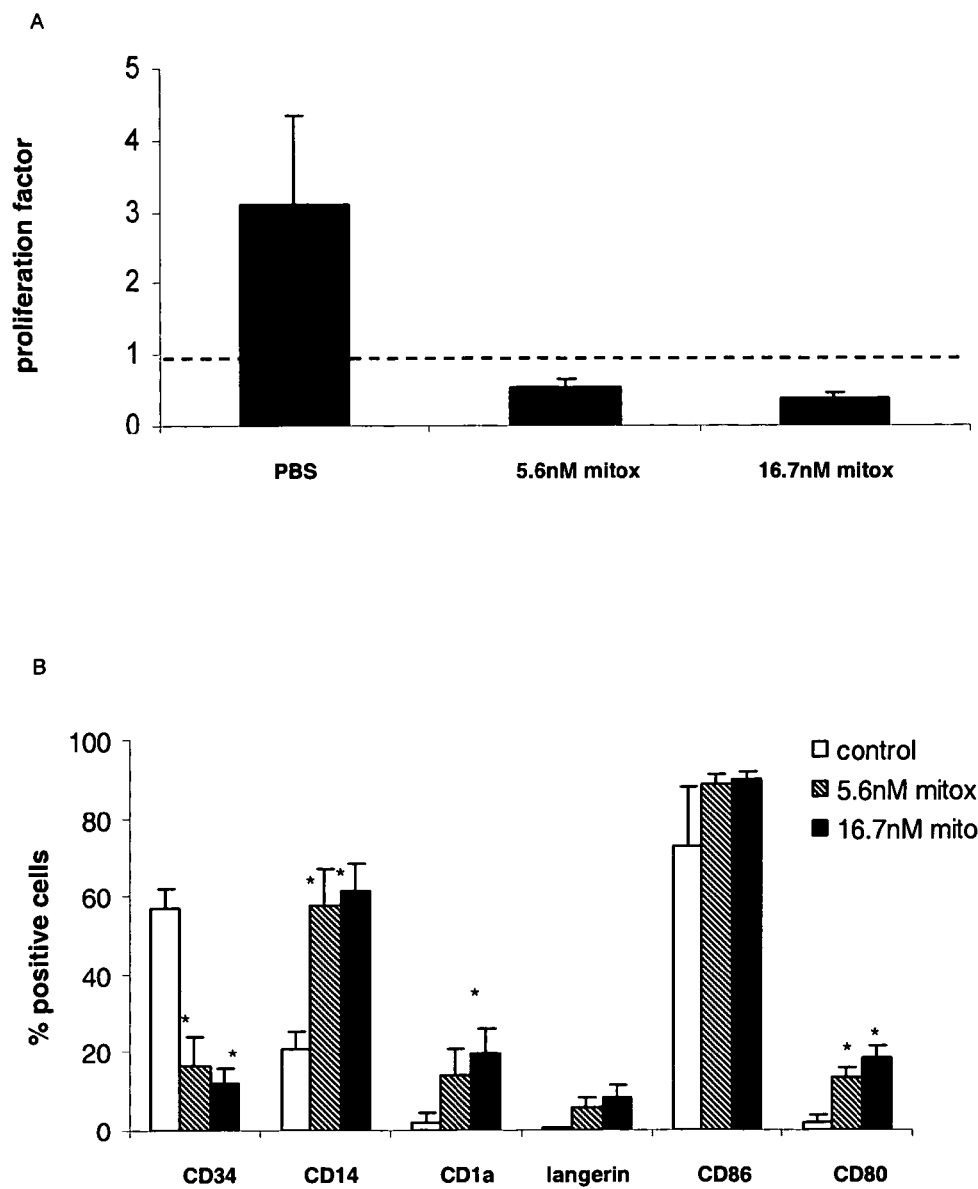

The present invention relates to a method for the production of functional dendritic cells wherein CD34 positive cells are contacted with compounds inducing and accelerating the differentiation of these CD34 positive cells into functional dendritic cells. More in particular, the CD34 positive cells are contacted with anthracyclines and/or anthracenediones. In another aspect, the current invention relates to the cells obtainable by the method according to the invention. In a further aspect the current invention relates to the use of compounds such as anthracyclines and/or anthracenediones that induce and accelerate the differentiation of CD34 positive cells into functional dendritic cells in the manufacture of a medicament for inducing an immune response in human in need thereof.

BACKGROUND OF THE INVENTION

Dendritic cells (DC) are the most powerful antigen presenting cells (APC) and play a pivotal role in initiating the immune response. In light of their unique properties, DC have been proposed as a tool to enhance immunity against infectious agents and in anticancer vaccine strategies. In the last few years, the development of DC has been extensively investigated.

Among professional antigen presenting cells (APC), DC are specialized in picking up and processing antigens into peptide fragments that bind to major histocompatibility complex (MHC) molecules. Located in most tissues, DC migrate from the periphery to secondary lymphoid organs such as the spleen and the lymph nodes, where antigen specific T lymphocytes recognize, through the T cell receptor, the peptide-MHC complexes presented by DC. While other professional and non-professional APC can only stimulate activated or memory T cells, DC have the unique capacity to prime naive and quiescent T lymphocytes.

Given their pivotal role in controlling immunity, the therapeutic role of DC has been proposed for many diseases that involve T-cell activation, such as autoimmune diseases and neoplastic disorders. Ex vivo pulsing with tumour antigens and the subsequent reinfusion of DC can lead to protection against tumours in animals. To address the efficacy of DC-based tumour immunotherapy strategies in humans, several clinical trials involving DC are currently in progress.

DC develop from hematopoietic precursor cells in the bone marrow, going through sequentially different stages of differentiation such as intermediary precursor cells in blood and immature DC in peripheral tissues and organs (Banchereau et al. 2000, Ann. Rev. Immunol. 18, 767-811). Once having reached the tissue, immature DC assume an important sensor function which is characterized by a high active uptake of antigens from the surrounding medium. Following stimulation by external signals ("danger signals") such as bacterial or viral infections or inflammatory processes, the DC migrate into the peripheral lymphatic organs, there undergoing differentiation into mature DC, and activating T cells by presenting antigens.

DC can be obtained by differentiating progenitor cells under influence of various molecules. For example, murine bone marrow (BM)-derived progenitor cells could differentiate into myeloid DC in presence of granulocyte-macrophage colony-stimulating factor (GM-CSF). In humans, the addition of tumour necrosis factor-$\alpha$ (TNF-$\alpha$) to GM-CSF and IL-4 was shown to induce the development of DC from bone marrow, cord blood (CB) and peripheral blood (PB) purified CD34 positive cells (CD34+ cells).

Jacobs et al (Horm Metab Res. 2008 February; 40(2):99-107) has given an overview of dendritic cell subtypes and in vitro generation of dendritic cells. The article describes the identification of different DC subpopulations including phenotypical and functional differences and describes recent developments on protocols for generation of DC. It describes that various cytokines and transcription factors are known to be responsible for the development of DC subpopulations. Depending on the subpopulation and the maturation state of these cells, they are either able to induce a broad cytotoxic immune response, and therefore represent a promising tool for anticancer vaccination therapies in humans or induce immune tolerance and are important within the context of autoimmunity.

Cytokines are small secreted proteins which mediate and regulate immunity, inflammation, and hematopoiesis. They are produced de novo in response to an immune stimulus. They generally (although not always) act over short distances and short time spans and at very low concentration. They act by binding to specific membrane receptors, which then signal the cell via second messengers, often tyrosine kinases, to alter its behavior (gene expression). Responses to cytokines include increasing or decreasing expression of membrane proteins (including cytokine receptors), proliferation, and secretion of effector molecules.

Cytokine is a general name; other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on the cells that secrete them (autocrine action), on nearby cells (paracrine action), or in some instances on distant cells (endocrine action).

It is common for different cell types to secrete the same cytokine or for a single cytokine to act on several different cell types (pleiotropy) Cytokines are redundant in their activity, meaning similar functions can be stimulated by different cytokines. Cytokines are often produced in a cascade, as one cytokine stimulates its target cells to make additional cytokines. Cytokines can also act synergistically (two or more cytokines acting together) or antagonistically (cytokines causing opposing activities). Their short half life, low plasma concentrations, pleiotropy, and redundancy all complicated the isolation and characterization of cytokines.

Cytokines are made by many cell populations, but the predominant producers are helper T cells (Th) and macrophages. The largest group of cytokines stimulates immune cell proliferation and differentiation. This group includes Interleukin 1 (IL-1), which activates T cells; IL-2, which stimulates proliferation of antigen-activated T and B cells; IL-4, IL-5, and IL-6, which stimulate proliferation and differentiation of B cells; Interferon gamma (IFNg), which activates macrophages; and IL-3, IL-7 and Granulocyte Monocyte Colony-Stimulating Factor (GM-CSF), which stimulate hematopoiesis.

In addition to GM-CSF and TNF-$\alpha$, a broad spectrum of cytokines has been shown to influence DC progenitor growth and differentiation. Early acting growth factors, such as stem cell factor (SCF) and Flt-3 ligand (Flt-3L) sustain and expand the number of DC progenitors whereas IL-3 in combination with GM-CSF has been shown to enhance DC differentiation. Moreover, transforming growth factor (TGF)-beta1 potentiates in vitro development of Langerhans-type DC.

In certain human dendritic lines like for instance the cell line MUTZ3, cells differentiate to DC under influence of cytokines like GM-CSF, IL-4 and TNF-alpha, whereas GM-CSF, TGF-beta1 and TNF-alpha also potentiates in vitro development of Langerhans-type DC.

Soluble factors, such as vascular endothelial growth factor (VEGF) and IL-6, inhibit the differentiation of CD34 positive progenitors into DC and redirect their development towards monocyte macrophage lineage. It is noteworthy that all these inhibitory soluble factors are secreted by cancer cells suggesting that prevention of DC development from CD34+ cells may be a mechanism of tumour escape from the immune response.

Although knowledge is accumulating with respect to how different progenitors differentiate under influence of different compounds, like cytokines to various types of DC, typically however, culturing time is long. For example, CD34 positive cells generally give rise to acceptable numbers of DC after for example 14 days of liquid culture in presence of GM-CSF plus TNF-α.

As discussed above, DC may be applied in the treatment of various diseases, including tumour diseases, infectious diseases, and autoimmune diseases. However, when DC recovered from primary cells are to be used in such treatment, the efficacy of the treatment can be severely hampered as DC or their precursor cells can only be obtained from patients or donors in very low quantities. Moreover, with the current methods, recovery requires much time and use of expensive reagents whereas the yield of obtained DC may be very small.

DC have been obtained from precursor cells, such as CD34 positive stem cells or monocytes, maturing in vitro by suitable stimulation with stimulatory molecules to form DC, although such precursor cells are extremely rare both in blood and tissue.

There is great interest in active specific immunotherapy with DC-based therapeutic vaccines for cancer. DC are intensively investigated as cellular adjuvants to harness the immune system to fight off cancer (see for example Bull Cancer. 2008 Mar. 1; 95(3):320-6.)

EP1419240 discloses the use of a cell line, MUTZ3, that can be differentiated into dendritic cells and that can be used as immunotherapeutic agent or as part of immunotherapeutic agents in the treatment of immune diseases. Although such cell line might solve the problem of the availability of sufficient cells, experimental data shows that it still requires at least 6 to 7 days of culturing under the correct conditions to obtain immature DC and at least 2 additional days for obtaining mature DC, requiring expensive cytokines to be used.

WO2006/012359 discloses a method for inducing differentiation of blood monocytes into functional antigen presenting dendritic cells. In short the cells are treated by physical perturbation, optional in the presence of for example disease effector agents.

EP1389234 discloses another method for differentiating lymphoid dendritic cells from human hematopoietic stem cells. The cells are differentiated in two steps, in a first medium comprising GM-CSF and in a second medium containing IFN-gamma. Culturing may take up to two weeks.

WO2008/036421 describes the use of an extract of reishi to increase the expression of (immature) dendritic cell markers like CD1a and CD83 in a human subject.

WO2008/02882 describes a method for producing Langerhans cells or interstitial dendritic cells from CD14 positive monocytes comprising placing said monocytes in the presence of a cell environment comprising epithelial cells and the like.

WO2004/076651 describes a method for differentiating monocytic dendritic cell precursors into immature dendritic cells comprising contacting non-activated dendritic cell precursors with a medium supplemented with GM-CSF in the absence of additional cytokines.

WO2004/083392 discloses a method for inducing differentiation of monocytes in blood into functional dendritic antigen presenting cells, using forces resulting from flow of monocytes through an apparatus having plastic channels.

US2004/0009596 describes the use of an extract from an Indian green mussel for differentiation and maturation of dendritic cells, and the extract is suggested as a replacement of GM-CSF.

US2005/0008623 describes the use of CD14 positive monocytes for obtaining various dendritic cell types. Differentiation is effected by GM-CSF and TGFbeta 1 (and IL13).

From the above it will be clear to the person skilled in the art there is need for further improvement of the available methods for the production of DC from progenitor cells. In particular there appears to be a need for methods allowing accelerated differentiation (and maturation) of DC, thereby shortening the time required for culturing and consequently reducing costs of such culturing by reducing the amount of media and for example cytokines required to obtain such functional DC.

SUMMARY OF THE INVENTION

The above-mentioned problem is solved by the subject matter as set-out in any of the accompanying claims.

It has surprisingly been found that CD34 positive cells can be differentiated and optionally subsequently matured into various DC within a time period that is advantageously shorter in comparison to methods known in the art.

In particular, the above-mentioned problem is solved by a method for the production of dendritic cells wherein CD34 positive cells are contacted with an anthracycline and/or an anthracenedione. In this way an accelerated production is achieved in comparison with methods according to the prior art which do not contact cells with an anthracycline and/or an anthracenedione.

With the method according to the invention, differentiated cells can thus be obtained in shorter periods of time, which may be important for the use of these cells in immunotherapy with DC-based therapeutic vaccines.

The cells obtainable by the method according to the invention were found to exhibit an increased expression of HLA-DR. The present invention therefore also provides novel dendritic cells obtainable by the method according to the invention wherein said dendritic cells have an increased expression of HLA-DR.

The invention also relates to the treatment of diseases wherein a composition comprising anthracyclines and/or anthracenediones is administered to a patient in need thereof. Such patients may suffer from various immunological diseases as well as cancer. In case of the treatment of cancer, the composition may be administered intradermally for optimal effects in terms of DC maturation and subsequent T cell activation.

The invention therefore relates to a composition comprising an anthracycline and/or anthracenedione for use in the treatment of immunological disorders.

The invention also relates to a composition comprising an anthracycline and/or anthracenedione for use in the treatment of cancer, wherein the anthracycline and/or anthracenedione is in a form suitable for intradermal injection

DETAILED DESCRIPTION OF THE INVENTION

The invention provides a method for the production of dendritic cells wherein CD34 positive cells are contacted with an anthracycline and/or an anthracenedione.

The person skilled in the art knows the meaning of the term "CD34 positive cells". It refers to primary cells or cell lines expressing CD34 on the cell surface. Such cells are known for their ability to differentiate into DC.

The term "contacting" or "contacted" is to be understood as that the cells are in physical and direct contact with the anthracycline and/or anthracenedione and allowed to interact for a time sufficient for the anthracycline and/or anthracenedione to induce and/or exhibit their accelerating effect. In practice, for example, the anthracycline and/or anthracenedione can be added to the culture medium used to maintain and/or grow and/or differentiate the CD34 positive cells into a DC.

Anthracyclines and anthracenediones are known to the person skilled in the art. Anthracyclines as well as anthracenediones inhibit DNA and RNA synthesis by intercalating between base pairs of a DNA/RNA strand, thus preventing the replication of rapidly-growing cancer cells. They also create iron-mediated free oxygen radicals that damage DNA and cell membranes. Anthracyclines and anthracenediones are also capable of inhibiting topoisomerase II enzymes, preventing the relieving of torsional stress in DNA during DNA replication.

In structural terms, Anthracyclines and anthracenediones may be defined as molecules comprising an anthraquinone structure as depicted in the following formula 1:

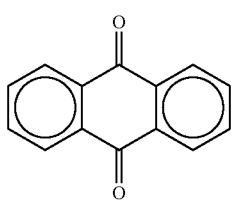

Formula 1

The basic anthraquinone unit can be decorated with various side chains. The skilled person will know the exact positions where such side chains may be attached to obtain functionally active anthracyclines and anthracenediones. Procedures for the synthesis of functional anthracyclines and anthracenediones are also known in the art. In vitro test systems for determining the functionality of anthracyclines and anthracenediones are also available in the art.

The invention also relates to the use of anthracycline and anthracenedione analogues. Such analogues are comprised within the term anthracyclines and anthracenediones and such analogues may consist of chemically modified structures of anthracyclines and anthracenediones as described and exemplified herein which still retain their original functionality.

Well-known members of the family of anthracyclines and anthracenediones are compounds with a tetrahydronaphthacenedione ring structure attached by a glycosidic linkage to an amino sugar, for example daunosamine.

Structures of some important anthracyclins such as daunorubicin and doxorubicin are shown below.

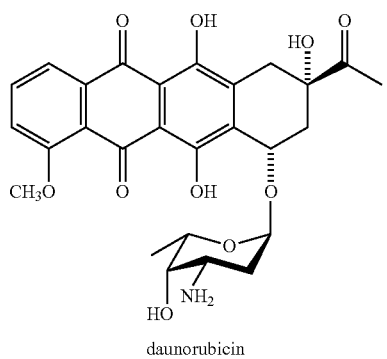

daunorubicin

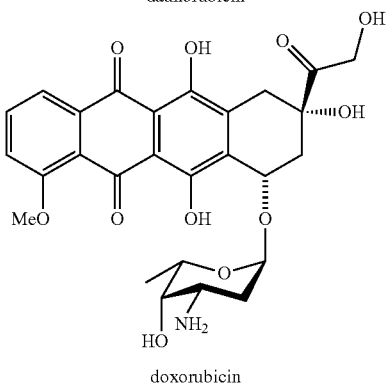

doxorubicin

Anthracenediones also comprise a basic anthraquinone structure. The anthracene ring can be substituted in any position except on the ketone groups. The molecular structure of mitoxantrone, the clinically most important anthracenedione is shown below.

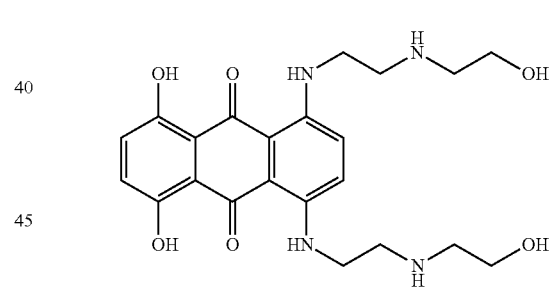

mitoxantrone

The method according to the invention provides the advantage that, as a consequence of shorter culturing time required, the need for chemicals like cytokines and growth medium and the like is reduced, making the production of the cells less costly and requiring less chemicals to be used and disposed of.

The person skilled in the art will understand that the method according to the invention may preferably be performed using isolated cells in a culture medium, i.e. by culturing cells using common techniques in the field, and as for example shown in the examples.

The term "isolated cells" in this respect is to be understood as cells that are isolated from their natural environment, preferably cells that are of the same lineage, phenotype and/or genotype, such as cultured cells or cell lines.

The invention therefore relates to a method as described above, wherein isolated CD34 positive cells are contacted with an anthracycline and/or an anthracenedione in a culture medium.

Examples of anthracyclines and anthracenediones that may advantageously be used in the method according to the invention include daunorubicin, doxorubicin, pirarubicin, aclarubicin, epirubicin, oxaunomycin, idarubicin and mitoxantrone.

A preferred method according to the invention is a method wherein the anthracycline and/or an anthracenedione is selected from the group consisting of daunorubicin, doxorubicin, pirarubicin, aclarubicin, epirubicin, oxaunomycin, andidarubicin and mitoxantrone.

Mitoxantrone, daunorubicin and doxorubicin are the preferred compounds to be used.

In general, any period of contacting the cells with an anthracycline and/or an anthracenedione, and which reduces the time required for obtaining dendritic cells in comparison to the circumstance wherein the cells would be cultured in the absence of said anthracycline, is a suitable period for contacting the cells. Such period of contacting may be easily determined by the person skilled in the art, for example by simply comparing the time that is required to obtain a certain development stage of the dendritic cell in the absence of said anthracycline with the time required to obtain the same development stage in the presence of said anthracycline.

In a preferred embodiment of the method according to the invention, the CD34 positive cells are contacted with an anthracycline and/or an anthracenedione for a period of between 1 and 7 days, preferably between 1.5 and 5 days and even more preferably between 2 and 4 days.

It has been found that cells contacted with an anthracycline and/or an anthracenedione for the above described time, can differentiate into dendritic cells that can be fully functional, in less time than would be possible without the addition of anthracycline and/or an anthracenedione. This is further exemplified in the examples.

The cells obtained with the method according to the invention can be fully functional dendritic cells, as is witnessed from the examples. It is shown therein that matured cells obtained with the method according to the invention are functional with respect to for example migration towards CCL19 and CCL21 and inducing naïve T cell activation and proliferation.

Figure 4:
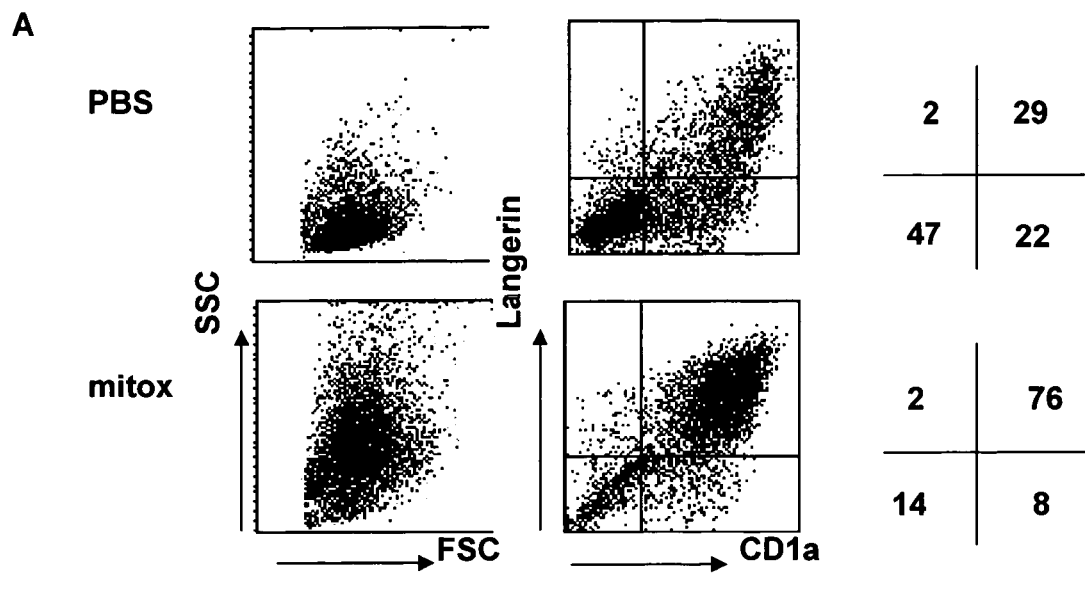
Figure 4:
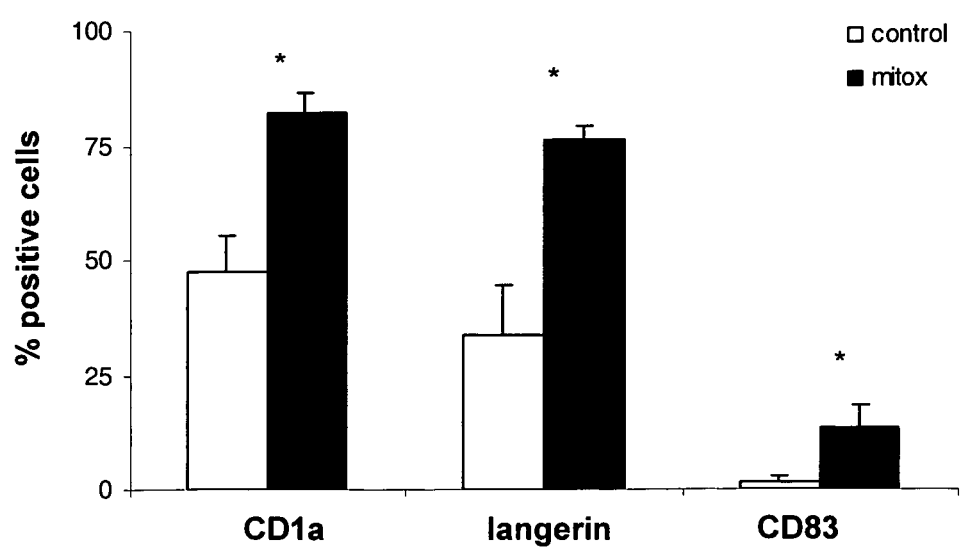

The above described accelerating effect may be obtained solely by contacting a CD 34 positive cell with an anthracycline and/or an anthracenedione, as is exemplified in FIGS. 1 and 4. However, the presence of an additional differentiation inducing compound like a cytokine also may contribute to the accelerated differentiation of the CD34 positive cells into various DC. Additionally, the presence of an additional compound capable of inducing maturation of the dendritic cells ensures quick maturation of the cells.

The person skilled in the art knows that the term "compound that is capable of inducing differentiation of the cells" or "differentiation inducing compounds" relates to such compound that, alone or in specific combination, can induce, when present in sufficient amounts in for example culture medium, the differentiation of dendritic precursor cell into or towards dendritic cells.

Well known examples include, but are not limited to, such chemical and biological molecules which influence the differentiation of cells, such as cytokines (IL-1b, IL-3, IL-4, IL-6, PGE-2, TNF-alpha, TGF-beta 1), growth factors (e.g. GM-CSF), and surrogate molecules for cytokines or growth factors inducing a biological effect comparable to that of the stimulatory molecules themselves, such as for example antibodies or other biological molecules such as LPS or polyIC.

The invention therefore relates to a method as described above wherein at least one compound capable of inducing differentiation of the dendritic cells is present in the culture medium. Advantageously, such a compound which is capable of inducing differentiation of the dendritic cells is selected from the group consisting of IL-1 b, IL-3, IL-4, IL-6, PGE-2, TNF-alpha, TGF-beta 1 and GM-CSF.

For example, fully differentiated dendritic cells were already obtained on day 4 when MUTZ3 cells were incubated with mitoxantrone in the presence of cytokines, whereas when MUTZ3 cells were cultured in the absence of such anthracycline but in the presence of cytokines, only at day 8-10 fully differentiated cells were obtained. This acceleration of differentiation as the consequence of the presence of anthracyclines in the system is also observed for CD34 positive progenitors isolated from a human subject.

Differentiation was also observed when CD34-positive precursor cells were incubated with only anthracyclines and/or anthracenediones, i.e. in the absence of cytokines. This is illustrated in FIG. 1B where it is shown that a CD34-positive precursor cell population differentiated into CD14-, CD1a-Langerin- and CD80-positive cells when exposed to mitoxantrone.

The person skilled in the art will understand that the cells may be contacted with the at least one compound which is capable of inducing cell differentiation either simultaneously with the anthracycline and/or anthracenedione (and which is preferred for practical reasons) or before or after the cells have been contacted with the anthracycline and/or anthracenedione. Although from practical viewpoint not preferred, it can even be envisaged that the contacting with the anthracycline and/or anthracenedione and the contacting with the compound capable of inducing differentiation towards dendritic cells occurs in an alternate fashion.

Particularly advantageous results have been obtained with a method according to the invention wherein the cells were contacted with at least one compound which is capable of inducing cell differentiation selected from the group consisting of GM-CSF (Granulocyte-macrophage colony-stimulating factor), TNF-alpha (Tumour Necrosis Factor Alpha), IL-4 (Interleukin 4), TGF-beta 1 (transforming growth factor beta) or combinations thereof.

Even more in particular, the combination of GM-CSF, IL-4 and TNF-alpha or the combination TGF-beta, GM-CSF and TNF-alpha can advantageously be used in the method according to the invention, that is, in combination with a anthracycline and/or anthracenedione, for example mitoxantrone, to obtain dendritic cells. Such cells can be obtained in a shorter period of time in comparison to a method wherein CD34 positive cells are not contacted with such anthracycline and/or anthracenedione.

In addition, the obtained cells have been proven to be fully functional as dendritic cells, as can be derived from the fact that the obtained cells migrate towards CCL19 and CCL21, promote T cell proliferation and antigen-specific T cell priming (see examples).

In order to obtain fully matured dendritic cells, the cells can also, after or at the time they are contacted with anthracycline and/or anthracenedione in a method according to the invention, be further treated with at least one compound selected from the group consisting of TNF-alpha, IL-6, PGE-2 or IL-1 beta or combinations thereof. Such treatment will allow obtaining mature dendritic cells from immature dendritic cells.

The person skilled in the art is aware of methods available in the art for obtaining mature dendritic cells from for example immature dendritic cells. For example, immature dendritic cells (including immature Langerhans-type dendritic cells) can be matured by adding TNF-alpha, IL-6, IL-1 beta and prostaglandin E2, although other methods known in the art to mature immature dendritic cells can likewise be employed.

The invention therefore relates to a method as described above wherein at least one compound capable of inducing maturation of the dendritic cells is present in the culture medium.

Maturation can be witnessed by, for example, expression of the maturation marker CD83 (Lechmann M, Berchtold S, Hauber J, Steinkasserer A (2002) The cells thus obtained are fully functional as dendritic cells as can be witnessed from the fact that the obtained cells migrate towards CCL19 and CCL21, and promote T cell proliferation (see examples).

It is therefore a preferred embodiment of the method according to the invention that the cells that are treated with an anthracycline and/or anthracenedione, and optionally with a further compound which is capable of inducing differentiation of the cells, are contacted with a compound that is capable of maturing immature dendritic cells, such as immature Langerhans dendritic cells.

Particularly advantageous results can thus be obtained with a compound selected from the group consisting of TNF-alpha, IL-6, IL-1 beta and prostaglandin E2, preferably when these compounds are used in combination (see examples).

In another preferred embodiment of the method according to the invention, the obtained dendritic cells are interstitial dendritic cells, plasmatoid dendritic cells, Langerhans dendritic cells, mature dendritic cells or immature dendritic cells.

The skilled person knows how to discriminate between such different types of dendritic cells, such a method is for example described in detail in US2004265998 and in the examples below.

For example, immature dendritic cells may be characterized by the induced expression of CD1a and/or DCsign, a major characteristic of immature dendritic cells on the surface of the cell. At the same time such cells may be characterized by the absence or low expression of CD83.

Langerhans cells are characterized by the expression of both langerin and CD1a, and can be induced under the influence of TGF-beta 1 (Caux et al. 1997, Blood 90 (4), 1458-1470).

Plasmacytoid dendritic cells are for example described by McKenna K, Beignon A, Bhardwaj N (2005). "Plasmacytoid dendritic cells: linking innate and adaptive immunity". J. Virol. 79 (1): 17-27. For example, they express BDCA2 (CD303) and/or CD123, whereas they are CDLCnegative.

In another preferred embodiment of the method according to the invention, the CD34 positive cells are CD34 positive MUTZ3 cells, CD34 positive human cells or CD34 positive tumour cells.

It has been found that these cells can advantageously be utilized in the method according to the invention.

MUTZ3 is a human cell-line model for cytokine-induced differentiation of dendritic cell from CD34 positive precursors and is described in detail in for example US2004265998.

CD34 positive cells from human, i.e. from human suffering from tumours, can be isolated from for example blood as described in the examples.

It has surprisingly been found that cell lines, like MUTZ3, and primary cells from human can advantageously be used as CD34 positive cells in the method according to the invention. Functional dendritic cells can thus be obtained, as can be derived from the fact that the mature cells obtained with a method according of the invention migrate towards CCL19 and CCL21, promote T cell proliferation and antigen-specific T cell priming. They also showed the characteristic expression of cell surface markers like for example CD83 of CD1a. Those cells could be obtained in a period that is significantly shorter in comparison to a method for obtaining such dendritic cells but not including contacting said CD34 positive cells with anthracycline and/or anthracenedione.

In a preferred embodiment of the invention, MUTZ3 cells are contacted with from 0.05 nM to 20 nM mitoxantrone and/or from 10 to 120 nM doxorubicin, in the presence of from 50 to 150 ng/ml GM-CSF, from 5 to 20 ng/ml IL-4 and from 0.5 to 4 ng/ml TNF-alpha. Such a method advantageously yields interstitial-type dendritic cells.

In another preferred embodiment of the invention, the MUTZ3 cells are contacted with from 0.05 nM to 20 nM mitoxantrone and/or from 10 to 120 nM doxorubicin, in the presence of from 5 to 20 ng/ml TGF-beta 1, from 50 to 150 ng/ml GM-CSF, and from 0.5 to 4 ng/ml TNF-alpha. Such a method yields Langerhans-type dendritic cells.

The characteristics and advantages of the cells thus obtained are shown in the examples below.

Also provided herein is a method wherein the cells are contacted with at least one anthracycline and/or an anthracenedione, preferably selected from the group consisting of daunorubicin, doxorubicin, pirarubicin, aclarubicin, epirubicin, oxaunomycin, andidarubicin and mitoxantrone and wherein the anthracycline and/or anthracenedione is applied to the cells at a concentration ranging from the IC20 concentration to the IC80 concentration, preferably ranging from the IC30 concentration to the IC70 concentration (as determined as set out in the examples).

In another aspect of the current invention there is provided for dendritic cells obtainable by the method according to the invention. These cells are characterized by and can be discriminated from such cells in the state of the art in that they exhibit an increased expression of HLA-DR, in comparison to cells obtained by the same method, but without contacting cells with an anthracycline. This is exemplified in the Examples section, and shown in FIG. 6.

The term "an increased expression of HLA-DR" is to be interpreted as meaning that the cells obtained by a method according to the invention have a higher expression of HLA-DR in comparison to cells cultured in a method according to the prior art, i.e. without the addition of an anthracycline and/or an anthracenedione. HLA-DR expression is an important factor with regards to T helper cells.

In another aspect, the invention provides the use of an anthracycline and/or anthracenedione, preferably selected from the group consisting of daunorubicin, doxorubicin, pirarubicin, aclarubicin, epirubicin, oxaunomycin, andidarubicin and mitoxantrone, in the manufacture of a medicament for treating immunological disorders in subjects in need thereof, in particular for treating immunological disorders by accelerating the immune response.

In other words, the invention provides a composition comprising an anthracycline and/or an anthracenedione for use in the treatment of immunological disorders.

It has now for the first time been found that when such anthracycline and/or anthracenedione is locally applied, e.g. by injection into a human body, and in particular in combination with the cytokines capable of inducing differentiation towards DC, a good, accelerated immune response can be induced in the human subject to be treated.

It is well known to the person skilled in the art that DC can be used in anti-cancer vaccines. As the cells obtained by the method according to the invention are fully functional and can be obtained in a shorter period of time, i.e. in an accelerated fashion, such cells (and the methods for obtaining such cells) are particularly advantageous in therapies directed to treating such cancers. In the treatment of cancers, the intradermal administration of the composition is preferred. This administration route is optimal, since it exposes the anthracycline and/or the anthracenedione directly to locally residing dermal dendritic cells as well as to lymph node dendritic cells via the lymphatic drainage. When administered via the conventional, intravenous route, the presence of overwhelming numbers of irrelevant cells such as red blood cells in the circulation prevent this effect.

The invention therefore relates to a composition comprising an anthracycline and/or anthracenedione for use in the treatment of cancer, wherein the anthracycline and/or anthracenedione is in a form suitable for intradermal injection.

Also in this aspect of the invention, it is preferred that the anthracycline and/or anthracenedione is selected from the group consisting of daunorubicin, doxorubicin, pirarubicin, aclarubicin, epirubicin, oxaunomycin, andidarubicin and mitoxantrone.

Also in this aspect of the invention, it is preferred that the composition further comprises a compound capable of inducing differentiation of CD34 positive cells, such as a compound selected from the group consisting of GM-CSF, TNF-alpha, IL-4, and TGF-beta 1.

In another aspect of the invention, there is provided for the use of the cells according to the invention or the use of the method according to the invention to obtain such cells, in anticancer vaccination therapies or auto-immune therapy. In other words, there is provided for use of cells according to the invention, or cells obtained form any of the methods according to the invention, or use of any of the methods according to the invention for the manufacture of a medicament for treatment of cancer or autoimmune diseases.

LEGEND TO THE FIGURES

FIG. 1: MUTZ3 progenitors were cultured for 72 hours in the presence of mitoxantrone and were analyzed for expansion (FIG. 1A) and for DC marker expression (FIG. 1B).

Figure 2:
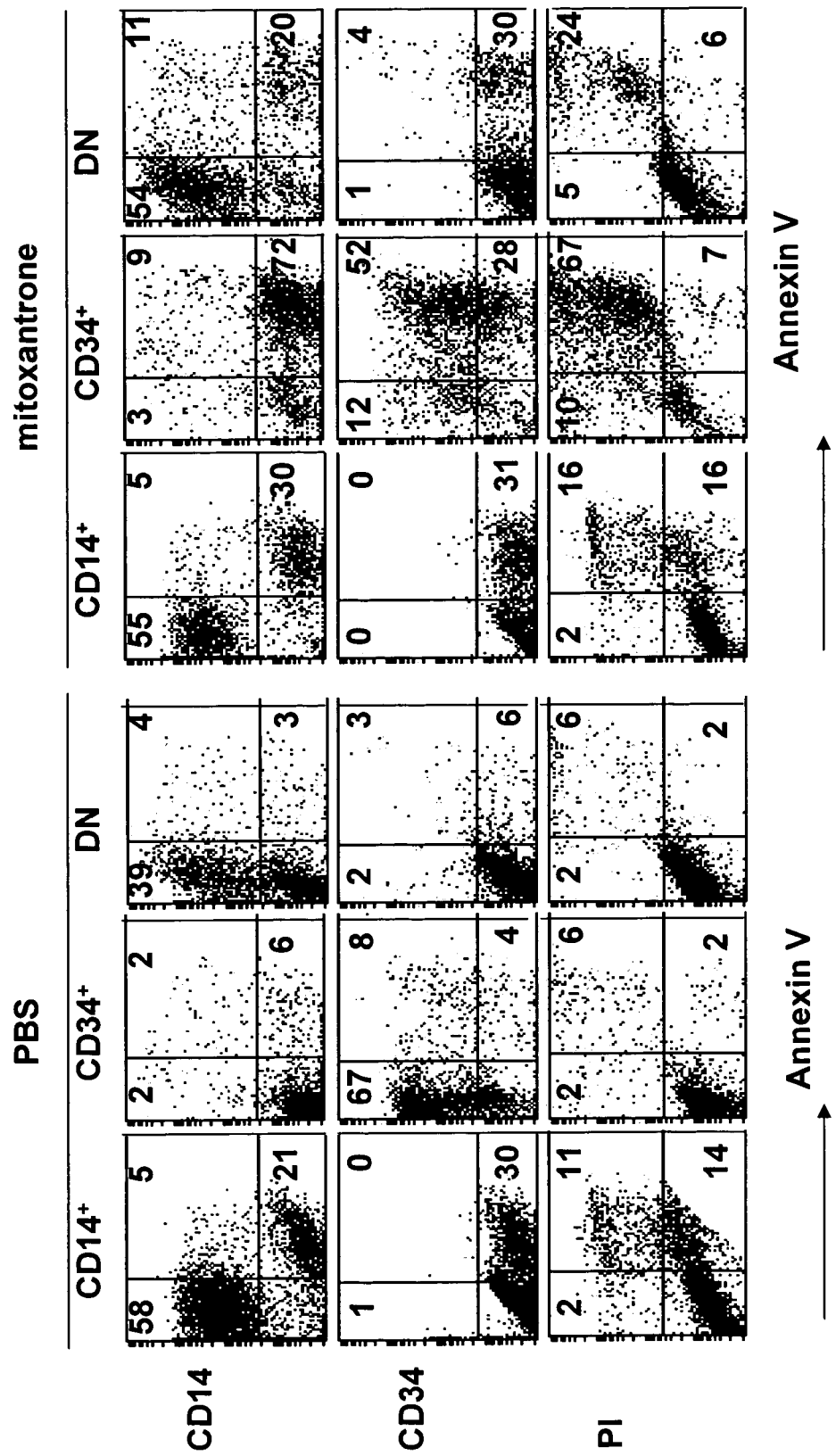

FIG. 2: Level of apoptosis and cell death upon PBS or mitoxantrone treatment within the three MUTZ3 subpopulations, which had been separated by CD14 or CD34 based magnetic bead sorting (MACS).

Figure 3:
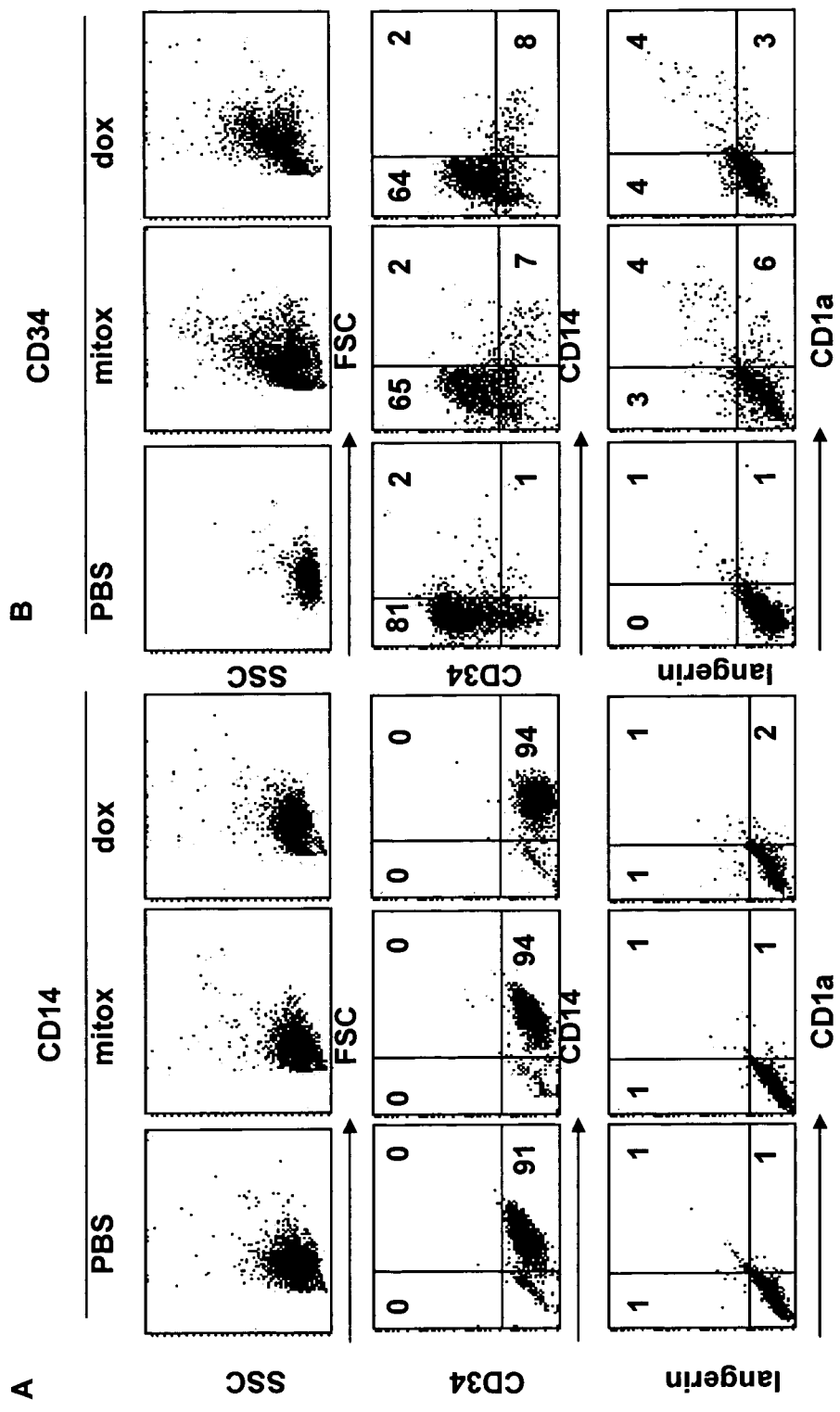
Figure 3:
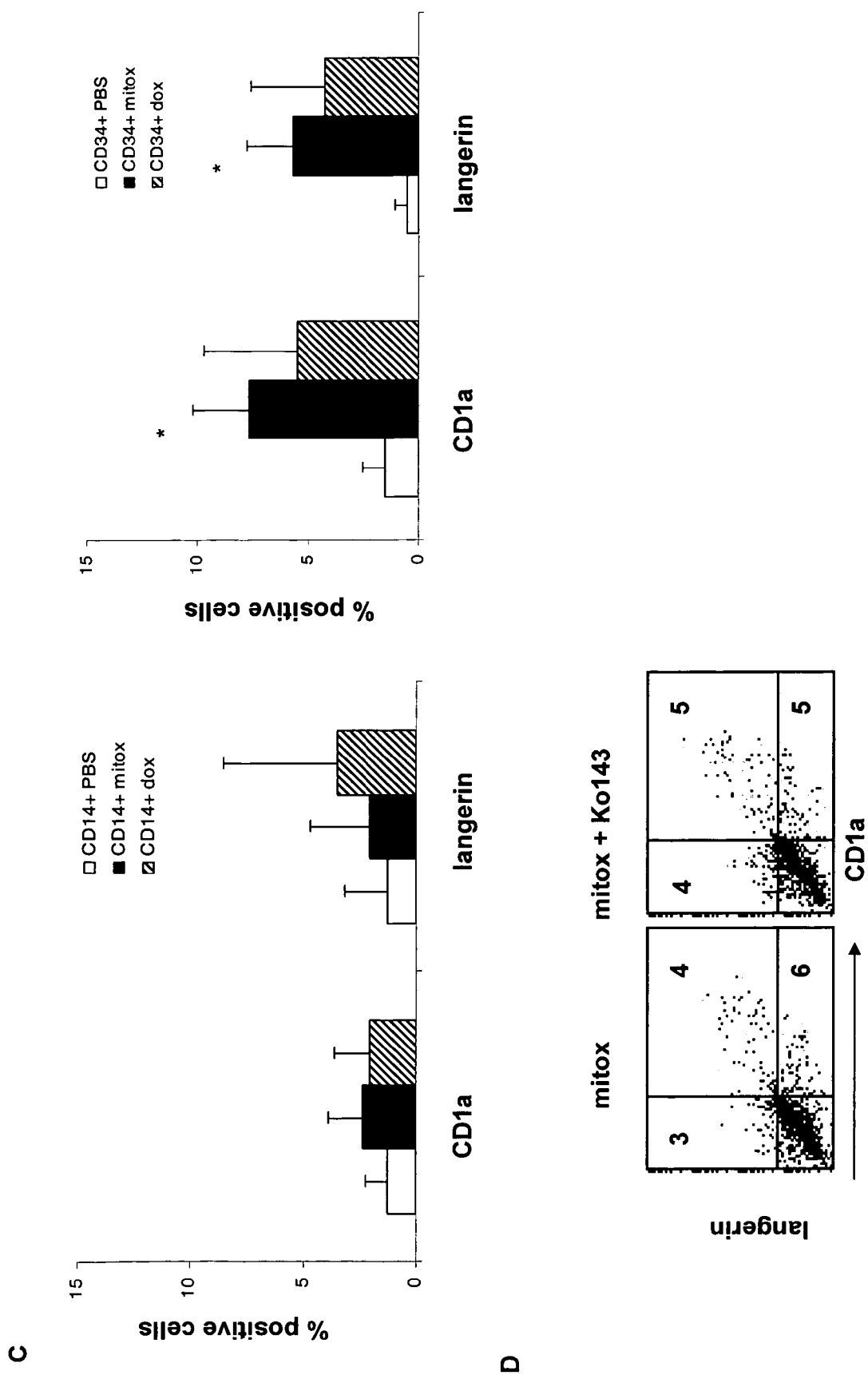

FIG. 3: Phenotypic analysis of the effects of mitoxantrone or doxorubicin on the MUTZ3 cells.

Figure 5:
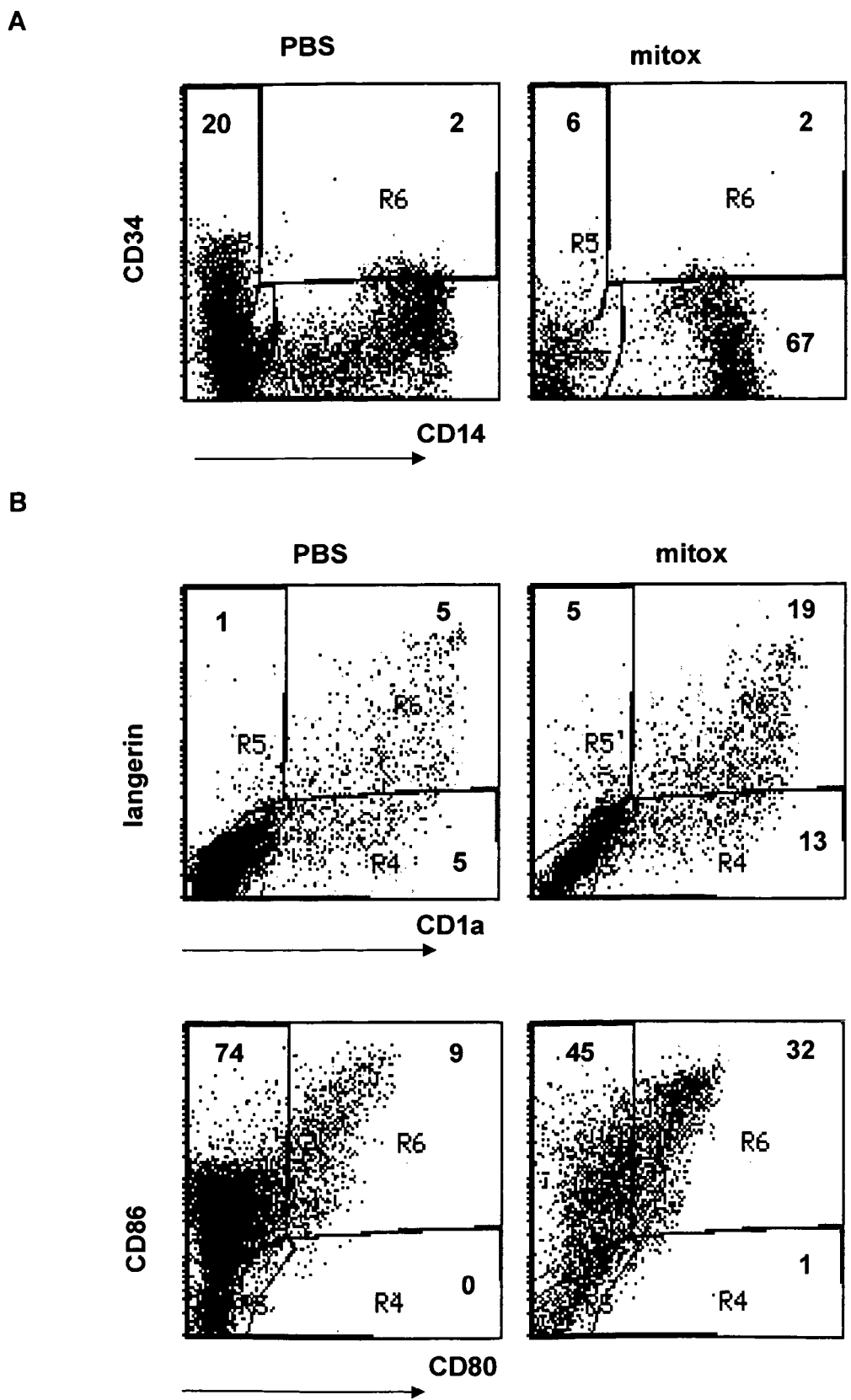

FIG. 4: FSC/SSC plots of day 4 LC cultured with PBS or mitoxantrone and CD1a/Langerin expression of these cultures FIG. 5: Mitoxantrone treatment resulted in the loss of most CD34 positive cells and an increase in CD14 positive cells (FIG. 5A). In the presence of LC-skewing cytokines, the addition of 16.7 nM mitoxantrone did induce a increase in the percentage of CD1a$^+$ Langerin$^+$ cells within 72 hours (FIG. 5B).

Figure 6:
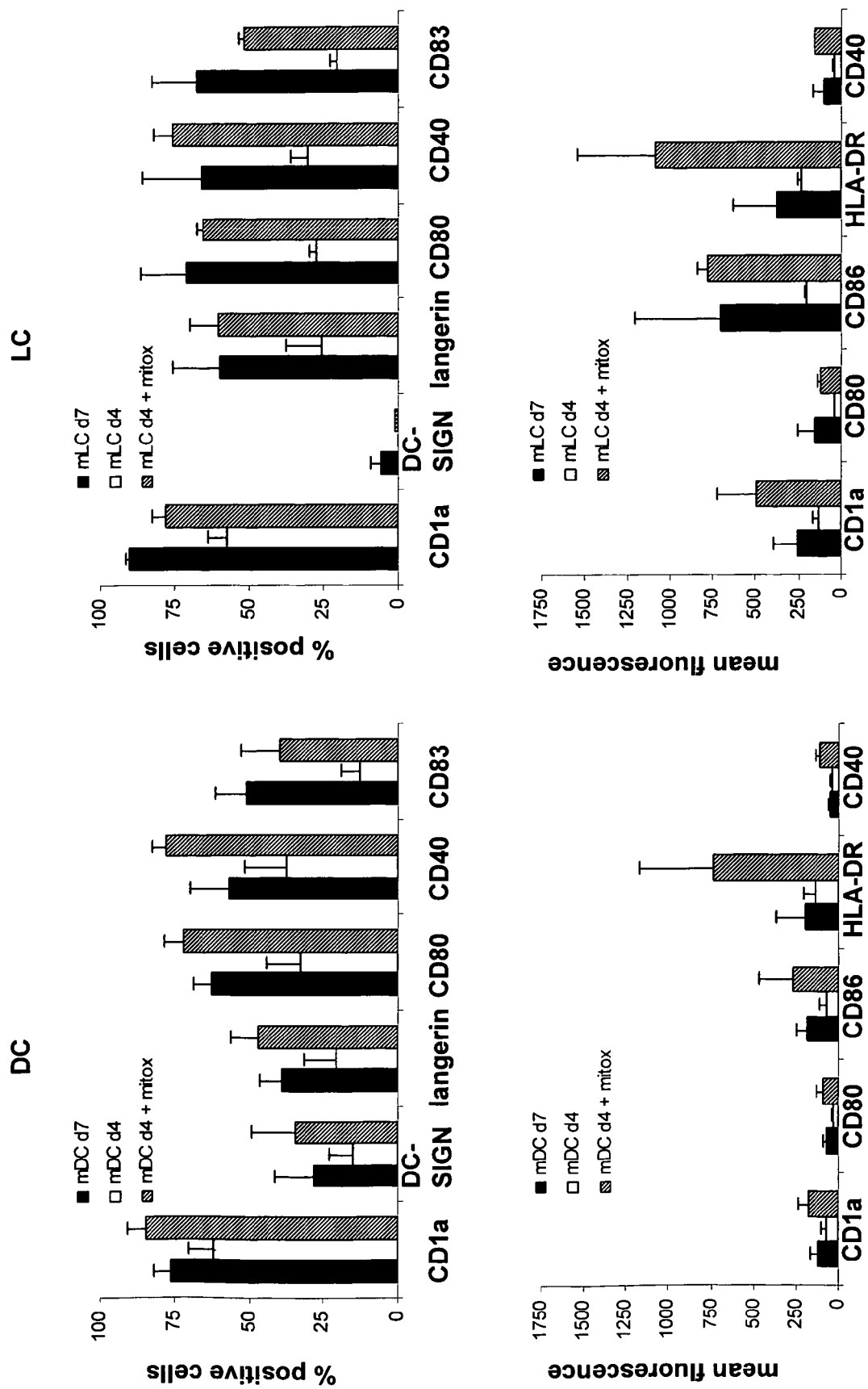

FIG. 6 shows the percentages of CD1a, DC-SIGN, Langerin, CD80, CD40 and CD83 expressing cells and the mean fluorescence intensities of CD80, CD86, CD40 and HLA-DR of mature day 7 MUTZ3-DC/LC and mature day 4 MUTZ3-DC/LC differentiated in the absence or presence of mitoxantrone.

Figure 7:
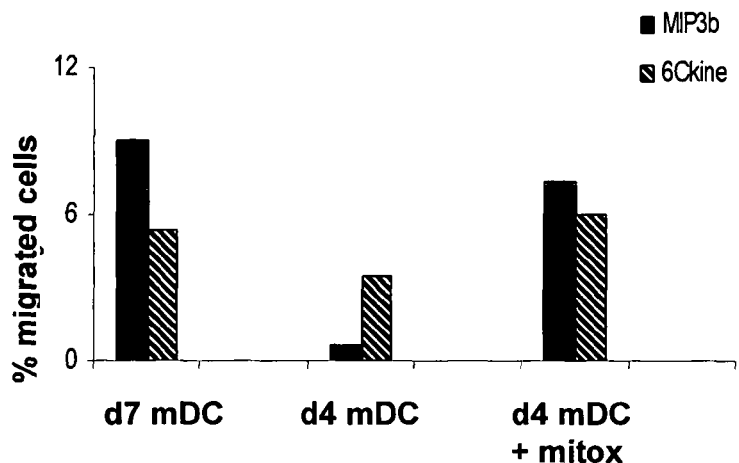
Figure 7:
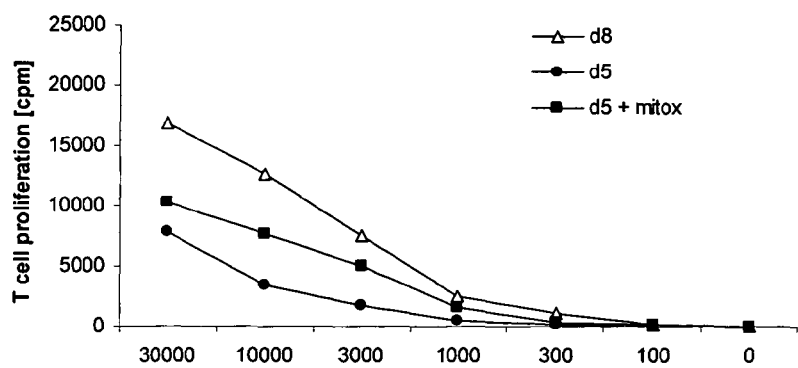
Figure 7:
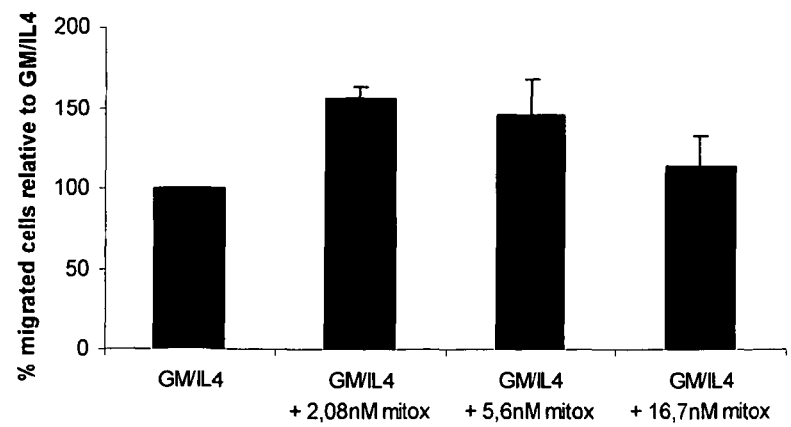

FIG. 7: MUTZ3-DC cultured in the absence or presence of mitoxantrone, were analyzed in a trans-well assay for their capacity to migrate towards the chemokines CCL19 and CCL21 (FIG. 7A) and were tested in a MLR for their capacity to stimulate T cell proliferation (FIG. 7B). Human skin biopsies were also analyzed for the ability of mitoxantrone to stimulate the migration of skin DCs (FIG. 7C).

Figure 8:
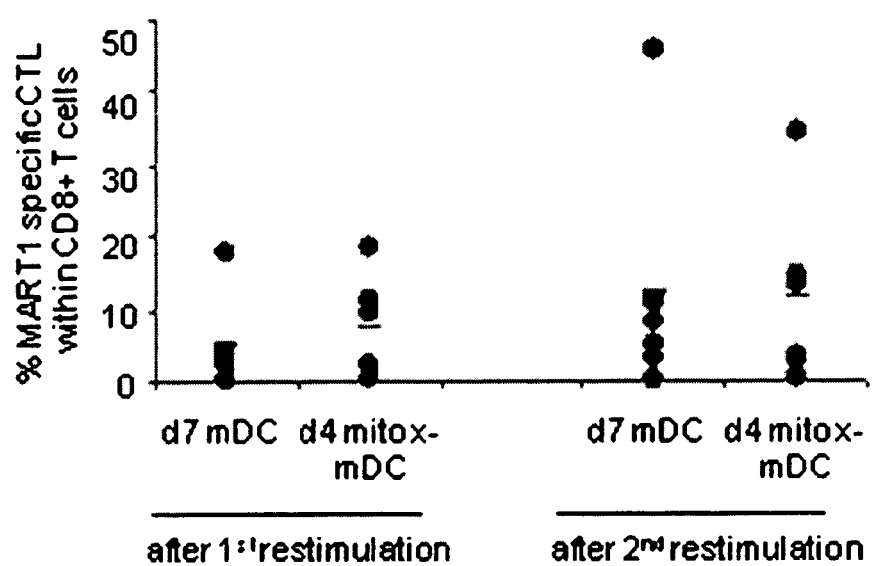

FIG. 8: MUTZ3-DC cultured in the presence of mitoxantrone for 4 days and control d7 MUTZ3-DC cultures, were analyzed for their capacity to prime tumor-antigen specific T cells. D7 MUTZ3-mDC and d4 mitox-mDC were loaded with MART1-peptides (26-35 L) and were analyzed for their capacity to prime MART1-specific CD8+ T cells within CD8 beta positive selected T cells from a HLA-A2 positive healthy donor. Six cultures were started with each DC cell type. After the primary peptide-loaded DC stimulation, T cells were restimulated with peptide-loaded DC after 10 and 17 days and the presence of MART-specific CD8+ T cells was analyzed by means of MART-tetramer staining after the first and the second restimulation. The percentages MART1-specific CD8+ T cells within each of the six cultures from the two DC types are depicted in the figure (represented by the dots). The d4 mitox-mDC were as capable as traditionally d7-mDC cultures in priming MART1-specific CD8+ T cells. The average percentage of MART1-specific CD8+ T cells within the six cultures is represented by the stripe.

EXAMPLES

Example 1

Materials and Methods

Chemicals:

All chemicals and drugs were obtained from Sigma Chemical Co. (St. Louis, Mo.) except for Ko-143 which was kindly provided by Dr. Allen (Netherlands Cancer Institute, Amsterdam, The Netherlands) and has been described before (van Loevezijn A., (2001) Bioorg. Med. Chem. Lett. 11, 29-32) and doxorubicin, which was purchased from Farmitalia Carlo Erba (Brussels, Belgium).

Cell Culture:

The AML-derived CD34+ MUTZ3 cell line was cultured as described before (Masterson A. J. (2002) Blood 100, 701-703.). In brief, MUTZ3 progenitors were cultured in MEM-alpha (Minimum essential medium, Gibco) containing 20% fetal calves serum (FCS), 100 IU/ml sodium-penicillin, 100 microg/ml streptomycin, 2 mM L-glutamine (pen/strep/glut), 50 microM beta-mercaptoethanol (2ME) and 10% 5637 conditioned medium (MUTZ3 routine medium) in 12-well plates (Co-star) at a concentration of 0.2 million cells/ml and were passaged twice weekly. LC were cultured in MEM-alpha containing 20% FCS, pen/strep/glut, 2ME and 10 ng/ml TGF-beta 1 (Biovision, Mountain View, Calif.), 100 ng/ml rhGM-CSF (Sagramostim, Berlex) and 2.5 ng/ml TNFalpha (Strathmann Biotec) (MUTZ3-LC medium) for 10 days in 12-well plates at a concentration of 0.1 million cells/ml, adding cytokines at day 0, 4 and 7. Interstitial DC were cultured in MEM-alpha containing 20% FCS, pen/strep/glut, 2ME and 10 ng/ml IL-4 (R&D), 100 ng/ml rhGM-CSF and 2.5 ng/ml TNFalpha (MUTZ3-DC medium) Where applicable, immature DC and LC were matured, respectively, by adding 50 ng/ml TNFalpha, 100 ng/ml IL-6 (Strathmann Biotec), 25 ng/mL-1 beta (Strathmann Biotec) and 1 microg/ml prostaglandin E2 (PGE2) (Sigma Aldrich) for 48 hours.

For mitoxantrone and doxorubicin cultures, 0.1-0.2 million cells/ml of MUTZ3 progenitors or CD34+, CD14+ and double negative (DN) magnetic bead sorted (MACS) MUTZ3 subsets (Miltenyi Biotec, Bergisch Gladbach, Germany) were seeded in 12-well plates in MUTZ3 routine medium or MUTZ3-DC/LC medium in the absence or presence of 1.04 nM, 2.08 nM, 5.6 nM, 16.7 nM mitoxantrone or 16.7 nM or 100 nM doxorubicin and were cultured for 72-96 hours before quantification of viable cells by trypan blue exclusion and phenotypic characterization by flowcytometry. DC and LC were matured (as above) on day 3 or 4 for 24 hours and were functionally tested in mixed leukocyte reaction or migration assays. In case of ABC transporter inhibition, 200 nM Ko-143 was added on day 0 to block BCRP activity.

CD34+Heamatopoietic Progenitor Cells

CD34+ heamatopoietic progenitor cells were isolated from blood and expanded for 2-5 weeks with 25 ng/ml fms-like tyrosine kinase-3 ligand (Flt3-L) and 10 ng/ml stem cell factor (SCF) as described previously (Bontkes H. J., de Gruijl T. D., Schuurhuis G. J., Scheper R. J., Meijer C. J., & Hooijberg E. (2002) Expansion of dendritic cell precursors from human CD34(+) progenitor cells isolated from healthy donor blood; growth factor combination determines proliferation rate and functional outcome. J. Leukoc. Biol. 72, 321-329.). To study the effect of mitoxantrone on these cells, thawed, expanded CD34+ progenitor cells were cultured with 16.7 nM mitoxantrone for 72 hours in the presence of 10 ng/ml Flt3-L and SCF (Stem Cell Factor). To study effects on LC differentiation, CD34+ progenitors were cultured with 16.7 nM mitoxantrone for 72 hours in the presence of 100 ng/ml GM-CSF, 10 ng/ml TGFbeta and 2.5 ng/ml TNFalpha. After 72 hours, phenotypic analysis was performed by flowcytometry.

Western Blotting

Cell pellets were lysed in ice-cold lysis buffer (1 mM EDTA; 1% NP-40; 1 mM PMSF), kept on ice for an hour, sonicated and stored at −20° C. until further use. Protein concentrations were determined with a Bio-Rad protein assay (Bio-Rad, Richmond, Calif.). Proteins were fractionated on an 8% polyacrylamide gel and subsequently transferred to nitrocellulose filter by electro blotting. For BCRP detection, filters were blocked (PBS containing 1% BSA, 1% milk powder and 0.05% tween-20) overnight and were subsequently incubated with the Bxp-53 (0.5 µg/ml) Mab (See for example J. Vet. Pharmacol. Ther. 2006 Vol 29(4) p 279-87) in blocking buffer for two hours. Immunoreactivity was visualized with rabbit-anti-rat immunoglobulin conjugated to HRP followed by color development with 0.5 g l$^{-1}$ 3,3'-diamino-benzidine tetrahydrochloride, 0.15 g l$^{-1}$ chloronaphtol and 0.02% H$_2$O$_2$ in PBS.

Flow Cytometric Immunophenotypical Analyses

Cells were immunophenotyped using the following FITC- and for PE-conjugated Mabs reactive against: CD1a (1:25), CD54 (1:25), CD80 (1:25), CD86 (1:25), CD40 (1:10) (PharMingen, San Diego, Calif.), CD14 (1:25), HLA-DR (1:25), DC-SIGN (1:10) (BD Biosciences, San Jose, Calif.), CD83 (1:10), CD34 (1:10), Langerin (1:10) (Immunotech, Marseille, France). In short, 2.5 to 5·10$^4$ cells were washed in PBS supplemented with 0.1% BSA and 0.02% NaN$_3$ and incubated with specific or corresponding control Mabs for 30 minutes at 4° C. Where applicable, AnnexinV and/or PI (Propidium iodide) were added after marker staining and 10 minutes prior to analysis. Cells were washed and analyzed on a FACS-calibur flow cytometer (Becton and Dickinson, San Jose, Calif.) equipped with CellQuest analysis software and the results were expressed as mean or median fluorescence intensity or the percentage of positive cells.

Mixed Leukocyte Reaction (MLR)

1·10$^2$-3·10$^4$ DC were co-cultured with 1·10$^5$ peripheral blood lymphocytes for 4 days in 96-wells plates in IMDM (Iscove's modified dulbecco's medium) containing 10% human pooled serum (HPS), pen/strep/glut and 2ME. At day 4, 2.5 µCi/ml [$^3$H]-thymidine (6.7 Ci/mmol, MP Biomedicals, Irvine, Calif.) was added per well for 16 hours. Plates were harvested onto glass fiber filtermats (Packard Instruments, Groningen, The Netherlands) using a Skatron cell harvester (Skatron Instruments, Norway), and [$^3$H]-thymidine incorporation was quantified using a Topcount NXT Microbetacounter (Packard, Meriden, Conn.).

In Vitro CTL-Priming

The in vitro priming of MART1 specific CTL was performed as described previously. (Santegoets SJAM. (2006) Cancer Immunol Immunother. 55, 1480-1490.) In short, mature d7 MUTZ3-DC and d4 mitox-DC, at a concentration of 1.0 million cells/ml, were loaded with 1 µg/ml MART1 26-35 L peptide in serum free IMDM for 3-4 hours in the presence of 3 µg/ml β2-microglobulin (β2M). After loading, cells were irradiated at 5000 rad, were washed and concentrated at 0.2 million cells/ml in Yssels medium (Yssel H. (1984) J Immunol Methods. 72, 219-227) supplemented with 2% hAB serum (ICN Biochemicals), pen/strep/glut, 2ME, 10 ng/ml IL6 and 10 ng/ml IL12 in 24-well plates. 0.1 million loaded DC were co-cultured with 1.0 million CD8β+ T cells, isolated from a HLA-A2+ donor by magnetic-bead sorting and 0.75-1.0 million, irradiated (5000 rad) CD8β− cells from the same donor, both diluted in Yssels medium. For each DC condition, 6 priming wells were started and the experiment was performed with 2 different HLA-A2+ donors. On day 10 and 19, CTL were re-stimulated with 10 ng/ml MART1 26-35 L loaded mature d7 MUTZ3-DC or d4 mitox-DC in the presence of 10 ng/ml IL-7. On day 12 and 21, 10 IU/ml IL-2 was added per well. MART1 tetramer (Tm) analysis was performed on CD8+ T cells on day 17 (after 1st restimulation) and 24 (after 2nd restimulation) using PE- and APC-labeled MART1 26-35 L Tm.

Statistical Analysis

Statistical analysis of the data was performed using the paired or unpaired two-tailed student's T-test. Differences were considered statistically significant when $p<0.05$.

Example 2

Sensitivity of MUTZ3 Progenitor Cells to Mitoxantrone

MUTZ3 progenitor cells were analyzed for their sensitivity to the cytostatic drug mitoxantrone. This drug is still being used in the clinic to treat several cancers or other diseases like multiple sclerosis and has been described to be a substrate for MDR-related ABC transporter. A 96 hour cytotox assay (Trypan blue exclusion) was performed to determine the IC50 value for mitoxantrone on MUTZ3 progenitors. MUTZ3 progenitor cells were sensitive to mitoxantrone with an IC50 value of 1.5±0.5 nM (n=3). (An example of such trypan blue assay is: place a suitable volume of a cells suspension in appropriate tube add an equal volume of 0.4% Trypan blue and gently mix, let stand for 5 minutes at room temperature. Place 10 µl of stained cells in a hemocytometer and count the number of viable (unstained) and dead (stained) cells. Calculate the average number of unstained cells in each quadrant, and multiply by 2*10$^4$ to find cells/ml. The percentage of viable cells is the number of viable cells divided by the number of dead and viable cells, and the IC50 can be determined)

Example 3

Mitoxantrone Induces Differentiation of MUTZ3 Progenitors

Studying the cytotoxic effects of mitoxantrone on the MUTZ3 progenitors, obvious morphological changes were observed at a concentration of 5.6 nM (IC60) and 16.7 nM (IC70) mitoxantrone. Hence, MUTZ3 progenitors were cultured for 72 hours in the presence of these concentrations and were analyzed for expansion (FIG. 1A) and for DC marker expression (FIG. 1B). The analysis revealed that, though dramatically compromising cell division, these doses of mitoxantrone drove the surviving MUTZ3 progenitors to differentiation, as there was an altered CD34$^+$/CD14$^+$ ratio in favor of the differentiating CD14$^+$ subset, mitoxantrone-treatment induced expression of the LC-specific markers CD1a and Langerin and increased expression levels of the costimulatory molecules CD86 and CD80 (FIG. 1B). Similar experiments were carried out with the drug doxorubicin. Like mitoxantrone, the IC70 concentration of doxorubicin (~100 nM) on MUTZ3 induced LC differentiation of MUTZ3 progenitors, whereas no effects were observed when 16.7 nM doxorubicin (equimolar concentration to mitoxantrone) was added.

FIG. 2 shows the level of apoptosis and cell death upon PBS or mitoxantrone treatment within the three MUTZ3 subpopulations, which had been separated by CD14 or CD34 based magnetic bead sorting (MACS). Little apoptosis or necrosis was present in the PBS controls (FIG. 2A). The CD14$^+$ population was not affected by mitoxantrone treatment, as a similar amount of CD14$^+$ Annexin V-positive cells was present after 72 hours of PBS or mitoxantrone treatment. The CD34$^+$, and to a lesser extent the DN population, was sensitive to the drug. However, despite cell death, a percentage of the proliferating CD34$^+$ cells survived the mitoxantrone treatment. Comparable results were obtained with 100 nM doxorubicin.

Example 4

CD34+, but not CD14+, MUTZ3 Cells Display Drug-Induced Differentiation

To see whether the skewing effect was due to CD34$^+$ cell death, automatically leading to an altered CD34$^+$/CD14$^+$ ratio or whether it induced differentiation of CD34$^+$ cells into CD14$^+$ cells and LC, isolated CD34$^+$ and CD14$^+$ cells were incubated with 16.7 nM mitoxantrone or 100 nM doxorubicin for 72 hours and were analyzed for differentiation induction.

Phenotypic analysis revealed that the effects of mitoxantrone or doxorubicin on the MUTZ3 cells could be contributed to the CD34$^+$ population (FIG. 3). CD14$^+$ cells were not affected by incubation with 16.7 nM mitoxantrone or 100 nM doxorubicin, as there were no alterations in the percentages of CD1a$^+$ or Langerin$^+$ cells between drug-treated cells and the PBS control (FIG. 3A). More CD14$^+$ cells were present in the cultures from CD34$^+$ cells upon treatment with both drugs (FIG. 3B) and drug-treatment resulted in the differentiation of CD34$^+$ sorted cells into CD1a$^+$ cells, of which approximately 50% also expressed the LC-marker Langerin (FIG. 3B). This differentiation effect could also be visualized by the forward/side scatter (FSC/SSC), as a clear shift in SSC could be noticed in the drug-treated CD34$^+$ cells, which was not present in drug-treated CD14$^+$ cells (FIGS. 3A and B). The graphs in FIG. 3C display the average induction of CD1a and Langerin expression within the two isolated subsets after 72 hours of PBS, mitoxantrone or doxorubicin treatment (n=3). No differences in CD1a or Langerin expression were observed within the CD14$^+$ subset between drug-treated and PBS-control samples. In the CD34$^+$ subset, incubation with 16.7 nM mitoxantrone lead to a significant increase in both CD1a and Langerin expression (p=0.02 for CD1a; p=0.03 for Langerin). Doxorubicin also induced CD1a and Langerin expression on CD34$^+$ MUTZ3 cells.

As mitoxantrone is the best known substrate for the ABC transporter BCRP (ABCG2), we ascertained whether the difference in sensitivity could be explained by a different expression level of BCRP between the three populations. No BCRP expression could be detected by Western blot analysis on CD14$^+$, CD34$^+$ or DN populations (data not shown). Also addition of the BCRP inhibitor Ko-143 could not abrogate the induction of CD1a and Langerin expression on CD34$^+$ MUTZ3 cells after mitoxantrone-treatment (FIG. 3D), suggesting that the observed effects were independent of BCRP activity.

Example 5

Mitoxantrone And Doxorubicin Accelerate LC Differentiation

Next we tested whether the addition of mitoxantrone or doxorubicin at the start of MUTZ3-LC cultures could boost differentiation. Addition of a single dose of 16.7 nM mitoxantrone at day 0 of MUTZ3-LC differentiation, resulted in fully differentiated cells with high expression of specific LC markers on day 4 whereas control cultures normally take 8-10 days to completely differentiate. In FIG. 4A FSC/SSC plots of day 4 LC cultured with PBS or mitoxantrone and CD1a/Langerin expression on these cultures are depicted. Clearly the mitoxantrone-treated LC had further differentiated as they displayed a more dendritic-morphology in the FSC/SSC plot and already 76% of the cells was CD1a$^{hi}$ Langerin$^+$ compared to 25% in the control cells. Besides CD1a and Langerin, these cells also showed enhanced expression of the co-stimulatory molecules CD80 and CD86 and had higher expression levels of HLA-DR and CD54. FIG. 4B shows combined data of 3 experiments for CD1a, Langerin and CD83. Besides the already mentioned significant increase in the percentage of cells expressing CD1a and langerin (p=0.02 and p=0.01 respectively), there was also a significant decrease in the percentage of CD14$^+$ and CD34$^+$ cells (p=0.04 and p=0.02, respectively) and a significant raise in the amount of cells expressing the maturation marker CD83 (p=0.03).

Example 6

CD34+ Heamatopoietic Progenitors Respond to Mitoxantrone

To establish whether human CD34$^+$ precursors from blood responded in a similar way to mitoxantrone as the CD34$^+$ MUTZ3 cells, CD34$^+$ heamatopoietic precursors isolated from human blood and expanded over a period of 1-4 weeks with Flt3Ligand (Flt3L), trombopoietin and stem cell factor (SCF) (Bontkes et al., J. Leukoc. Biol. 2002 Vol 72(2):321) were thawed from liquid nitrogen and treated with mitoxantrone. Mitoxantrone treatment resulted in the loss of most CD34$^+$ cells and an increase in CD14$^+$ cells (FIG. 5A). In the presence of LC-skewing cytokines, the addition of 16.7 nM mitoxantrone did induce a increase in the percentage of CD1a$^+$ Langerin$^+$ cells within 72 hours (FIG. 5B) (n=2). In contrast, when similar experiments were performed with CD14$^+$ monocytes isolated from blood, in analogy with the CD14$^+$ MUTZ3 data, there was no effect on cell viability, nor was any differentiation induction observed.

Example 7

Mitoxantrone-Cultured DC are Functional

With such differentiation-accelerating capacities, mitoxantrone could be a suitable adjuvant for fast in vitro differentiation of DC vaccines for immunotherapeutic vaccination strategies. Hence we analyzed whether the concentration of mitoxantrone could be reduced without losing the differentiation advantage, but with the advantage of higher viable cell yields. In MUTZ3-DC and -LC cultures, a 2-step titration of the 16.7 nM mitoxantrone concentration was performed and DC/LC phenotypes were analyzed after 72-96 hours. A robust effect on MUTZ3-DC and -LC differentiation was still observed when 2.08 nM mitoxantrone was added during differentiation. Interestingly, in the MUTZ3-DC cultures supplied with mitoxantrone, Langerin expression was increased, suggesting a LC-skewing capacity of mitoxantrone. FIG. 6 shows the percentages of CD1a, DC-SIGN, Langerin, CD80, CD40 and CD83 expressing cells and the mean fluorescence intensities of CD80, CD86, CD40 and HLA-DR of mature day 7 MUTZ3-DC/LC and mature day 4 MUTZ3-DC/LC differentiated in the absence or presence of mitoxantrone. In both cases, the addition of 2.08 nM mitoxantrone increased the amount of CD1a, Langerin, CD80, CD40 and CD83 expressing cells and also enhanced the expression levels of CD80, CD86, CD40 and HLA-DR. For HLA-DR expression was even higher than on the control cultures (FIG. 6).

If such mitoxantrone-generated DC are to be used for future vaccination strategies, they need to be functionally fully active. Therefore MUTZ3-DC cultured in the absence or presence of mitoxantrone, were analyzed in a trans-well assay for their capacity to migrate towards the chemokines CCL19 and CCL21 (FIG. 7A) and were tested in a MLR for their capacity to stimulate allogeneic T cell proliferation (FIG. 7B). Unlike the untreated mature day 4 DC, the day 4 mitoxantrone-generated DC were comparable to day 7 matured control DC in their capacity to migrate towards the LN-homing chemokines and were equipped to induce T cell proliferation.

Example 8

Mitoxantrone can Stimulate Human Skin DC Migration

To establish whether mitoxantrone could be beneficial as a local adjuvant, human skin explants were intra-dermally injected with GM-CSF and IL-4 in combination with 2.08 nM, 5.6 nM or 16.7 nM mitoxantrone and 6 mm punch biopsies were floated in medium containing the same concentration of mitoxantrone. Skin DC were allowed to migrate from the biopsies for 2 days, after which they were harvested, quantified and phenotyped. FIG. 7C shows that injection of 2.08 nM or 5.6 nM mitoxantrone increased the amount of migrated cells by approximately 50-60%. Injection of 16.7 nM mitoxantrone only slightly increased the amount of migrated cells, possibly due to the induction of cell death in the migrating or migrated DC.

In conclusion, the results show that high concentrations of the anthracyclines like the cytotoxic drugs mitoxantrone and doxorubicin can drive CD34$^+$ precursor cells to DC differentiation and that low concentrations of mitoxantrone can efficiently accelerate (in vitro) DC differentiation in combination with differentiating cytokines. These quickly differentiated, anthracycline-generated DC (day 4) were skewed towards a more LC-like phenotype and were as capable as conventional long-term cultured DC (day 7) in migrating towards the chemokines CCL19 and CCL21 and in promoting T cell proliferation. In addition, it was shown that intradermal injection of low dose of mitoxantrone in plain medium, but especially in combination with GM-CSF and IL-4, increased the amount of skin emigrating DC.

Example 9

Mitoxantrone-Cultured DC can Prime Antigen-Specific T Cells

A very crucial function of DC in anti-tumor vaccination strategies is the ability of the cells to prime tumor antigen-specific CTL. Hence d4 mitox-mDC and d7 MUTZ3-mDC were analyzed for their capacity to prime MART1-specific CTL in vitro. Both DC types were able to induce MART1-specific CTL, as analyzed by the presence of MART1-specific tetramer (Tm)-positive cells within the CD8+ T cell subset in the bulk cultures (FIG. 8). From the 12 bulk cultures in which CTL-priming was initiated, MART1 Tm+ CTL could be detected in 12/12 cultures primed with d4 mitox-DC compared to 11/12 cultures primed with d7 control MUTZ3-mDC. FIG. 5d shows the percentage of Tm+ CTL for 6 bulk cultures from one HLA-A2+ donor after the second re-stimulation with peptide-loaded DC.

The results thus show that anthracyclines s the cytotoxic drug mitoxantrone (and also doxorubicin) induce differentiation of surviving CD34$^+$ DC precursors. In addition, when added at the start of differentiation in combination with DC or LC-skewing cytokines, this drug dramatically enhanced differentiation.

Our data showed induction and acceleration of Langerhans cell differentiation upon treatment of CD34$^+$, but not CD14$^+$, precursor cells with anthracyclines like mitoxantrone despite causing cell death. The CD34$^+$ precursor cells were sensitive to the drugs, but this sensitivity was reduced when differentiation-inducing cytokines were present. Important for all in vitro cultured DC to be used for vaccination purposes, are the functional capacities of the DC. The anthracycline (e.g. mitoxantrone) generated DC, although only differentiated for 3 days and matured with a standard cytokine maturation cocktail for 24 hours, were fully capable of migrating towards the chemokines CCL19 and CCL21 and could efficiently induce T cell proliferation. This method of DC differentiation is thus a less time-consuming, more cost-effective method of generating in vitro cultured DC at (c)GMP levels for vaccination purposes.

In addition, the data show that local administration of anthracyclines like mitoxantrone, in combination with cytokines could induce efficient and enhanced DC migration from human skin explants. These findings show that anthracyclines like mitoxantrone are able to induce DC activation at peripheral sites, like skin (preferred vaccination site) or tumour, where DC activation or differentiation from local precursors may be suppressed. For example, in melanoma cutis, the site of the tumour is easily accessible and the anatomical location (skin) ensures the presence of targetable/druggable LC precursor cells. The abundant presence of tumour antigens, especially after local administration of cytostatic agents, which will induce some melanoma cells to die, and the fast induction of LC differentiation by the anthracyclines like mitoxantrone, may give rise to excellent anti-tumour immune responses.

The invention claimed is:
1. A method for the production of dendritic cells, the method comprising:
contacting CD34 positive cells with an anthracycline and/or an anthracenedione in a culture medium thereby increasing the rate of production of dendritic cells from the CD34 positive cells in comparison to CD34 positive cells not contacted with anthracycline and/or anthracenedione;

allowing the CD34 positive cells to develop into dendritic cells; and harvesting dendritic cells.

2. The method according to claim 1, wherein the anthracycline and/or an anthracenedione is selected from the group consisting of daunorubicin, doxorubicin, pirarubicin, aclarubicin, epirubicin, oxaunomycin, andidarubicin and mitoxantrone.

3. The method according to claim 1, wherein the CD34 positive cells are contacted with the anthracycline and/or an anthracenedione for a period of between 1 and 7 days.

4. The method according to claim 3, wherein the CD34 positive cells are contacted with the anthracycline and/or an anthracenedione for a period of between 2 and 4 days.

5. The method according to claim 1, further comprising contacting the cells with at least one additional compound able to induce differentiation of the CD34 positive cells into dendritic cells.

6. The method according to claim 5, wherein the at least one additional compound that is able to induce differentiation of the CD34 positive cells into dendritic cells is selected from the group consisting of GM-CSF, TNF-alpha, IL-4, and TGF-beta 1.

7. The method according to claim 1, wherein at least one compound able to induce maturation of dendritic cells is present in the culture medium.

8. The method according to claim 7, wherein the compound which is able to induce maturation of dendritic cells is selected from the group consisting of TNF-alpha, IL-6, PGE2 and IL-1Beta.

9. The method according to claim 1, wherein the dendritic cells are selected from the group consisting of interstitial dendritic cells, immature dendritic cells, Langerhans dendritic cells, plasmatoid dendritic cells, and mature dendritic cells.

10. The method according to claim 1, wherein the CD34 positive cells are MUTZ3 cells, human cells, or human tumor cells.

11. The method according to claim 10, wherein MUTZ3 cells are contacted with from 0.05 nM to 20 nM mitoxantrone and/or from 10 to 120 nM doxorubicin, in the presence of from 50 to 150 ng/ml GM-CSF, from 5 to 20 ng/ml IL-4 and from 0.5 to 4 ng/ml TNF-alpha.

12. The method according to claim 10, wherein MUTZ3 cells are contacted with from 0.05 nM to 20 nM mitoxantrone and/or from 10 to 120 nM doxorubicin, in the presence of from 5 to 20 ng/ml TGF-beta 1, from 50 to 150 ng/ml GM-CSF, and from 0.5 to 4 ng/ml TNF-alpha.

13. The method according to claim 1, wherein said dendritic cells have an increased expression of HLA-DR.

14. The method comprising according to claim 1, further comprising:

administering the harvested dendritic cells to a subject.

* * * * *

UNITED STATES PATENT AND TRADEMARK OFFICE
CERTIFICATE OF CORRECTION

PATENT NO.        : 8,470,789 B2                             Page 1 of 1
APPLICATION NO. : 12/736920
DATED             : June 25, 2013
INVENTOR(S)       : van Wetering et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 219 days.

Signed and Sealed this
Eighth Day of September, 2015

Michelle K. Lee
*Director of the United States Patent and Trademark Office*